United States Patent [19]

Kamiya et al.

[11] 4,421,720
[45] Dec. 20, 1983

[54] DETECTOR FOR CARBON MONOXIDE CONCENTRATION OF A GAS

[75] Inventors: Hideo Kamiya, Ekakushinmachi; Hiroshi Shinohara, Okazaki; Yasuhiro Otuka, Toyota; Mari Okazaki, Chiryu, all of Japan

[73] Assignee: Toyota Jidosha Kabushiki Kaisha, Toyota, Japan

[21] Appl. No.: 268,055

[22] Filed: May 28, 1981

[30] Foreign Application Priority Data

May 29, 1980 [JP] Japan ................................ 55-072611

[51] Int. Cl.³ ........................................... G01N 27/16
[52] U.S. Cl. ..................................... 422/97; 436/134; 436/152
[58] Field of Search .................. 436/134, 152; 422/94, 422/95, 96, 97, 98; 123/571; 60/276

[56] References Cited

U.S. PATENT DOCUMENTS

| | | | |
|---|---|---|---|
| 3,549,329 | 12/1970 | Silverman et al. | 422/98 |
| 4,043,305 | 8/1977 | Henault | 123/571 X |
| 4,123,225 | 10/1978 | Jones et al. | 422/98 |
| 4,164,539 | 8/1979 | Johnston | 422/96 |

FOREIGN PATENT DOCUMENTS

| | | | |
|---|---|---|---|
| 2746381 | 4/1978 | Fed. Rep. of Germany | 422/98 |
| 52-68494 | 6/1977 | Japan | 422/98 |

Primary Examiner—Arnold Turk
Attorney, Agent, or Firm—Oblon, Fisher, Spivak, McClelland & Maier

[57] ABSTRACT

Apparatus for the detection of carbon monoxide concentration of a gas. The apparatus comprises a base from which a pair of arms extend, a resistance layer disposed on each arm serving both to measure the difference in temperature between the arms and to heat a catalyst layer; a protective layer on the resistance layers to prevent electrical shorts caused by deposit of conductive particles in the gas to be detected; and a catalyst layer on one and only one of the arms in contact with the protective layer.

4 Claims, 7 Drawing Figures

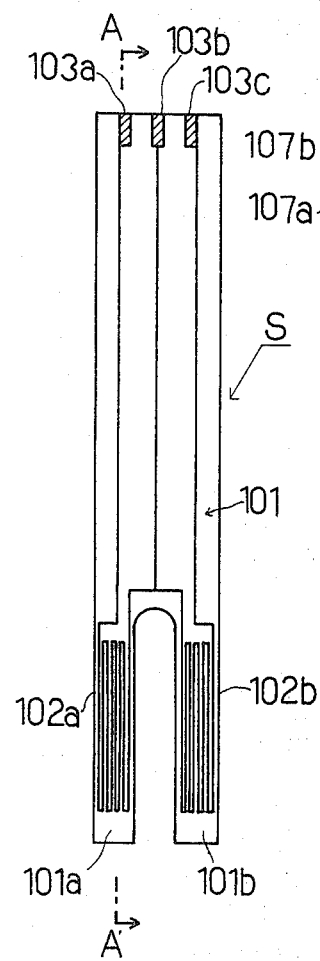
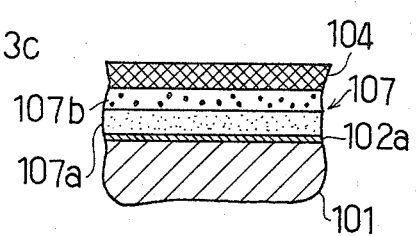
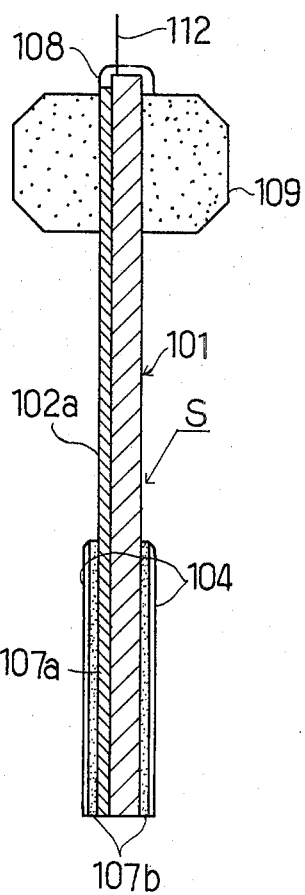
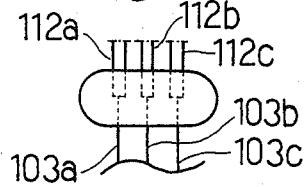
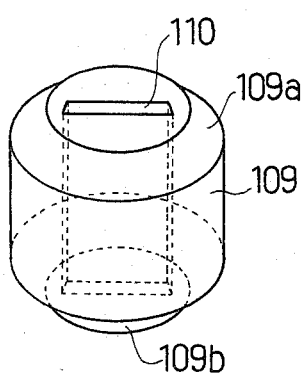

DETECTOR FOR CARBON MONOXIDE CONCENTRATION OF A GAS

BACKGROUND OF THE INVENTION

1. Field of the Invention

The instant invention relates to a new method of detecting the carbon monoxide concentration of a gas. More particularly, the instant invention relates to a new method of detecting the carbon monoxide concentration of a gas by using a resistance gas sensor which consists of a forked base from which a pair of arms extend, a resistance layer formed on said forked base, and a catalyst layer formed on one of said pair of arms.

Said gas containing carbon monoxide may be exhaust gas from a car engine or the like. An exhaust gas recirculating system (EGR system) in which a portion of the exhaust gas of the engine is recirculated to the intake side of the engine is a preferable system for decreasing the concentration of nitrogen oxide contained in a exhaust gas of the engine, especially the diesel engine. Nevertheless, the combustion of the intake gas in the engine may be incomplete if the recirculating volume of the exhaust gas, (i.e., the EGR ratio) becomes excessive. In this case, carbon monoxide concentration, smoke quantity, and the like in the exhaust gas may increase. Therefore it is preferable to detect the carbon monoxide concentration of the exhaust gas and to control the EGR ratio by this result.

2. Description of the Prior Art

Hitherto resistance gas sensors have been used to detect carbon monoxide. Such resistance gas sensors consist of a forked base from which a pair of arms extend. One of the arms is for reference, and the other arm is for detection. A linear resistance layer is formed on the surface of the forked base, a linear heating layer is formed on the backface and/or on the inside of the forked base, and a catalyst layer is formed on the surface of the arm used for detection.

In such a resistance gas sensor, the change of the resistance value is output. The change of the resistance value originates in the reaction heat of oxidation of carbon monoxide contained in the exhaust gas. Such oxidation may be caused to occur by contacting the exhaust gas with the catalyst layer of the resistance gas sensor. Carbon monoxide concentration is calculated from the output change of the resistance value. In such oxidation, free energy of activation may be supplied to the reaction by heating the heating layer of the resistance gas sensor. Nevertheless, as above mentioned, the heating layer is independent of the resistance layer in the traditional resistance gas sensor, so it is necessary to arrange a terminal for outputting from the resistance layer and a separate terminal for inputting to the heating layer. Therefore, in the prior art, separate processes are necessary to form the heating layer and the resistance layer, and separate terminals are necessary to output from the resistance layer and to input to the heating layer. The above mentioned complexities in the manufacturing process and in the structure may be a large disadvantage, especially for small resistance gas sensors for car use.

OBJECTS OF THE INVENTION

Accordingly, an object of the present invention is to provide a method of detecting the carbon monoxide concentration of a gas in which a resistance gas sensor having a simple structure may be used.

Another object of the present invention is to provide a method of detecting the carbon monoxide concentration of a gas in which a resistance gas sensor may be manufactured in a simple process.

A further object of the present invention is to provide a method of detecting the carbon monoxide concentration of a gas in which a resistance gas sensor having the accuracy and the durability suitable for car use is employed.

SUMMARY OF THE INVENTION

Briefly, these objects of the present invention can be attained by a new method comprising letting a gas containing carbon monoxide contact with a resistance gas sensor which consists of a forked base from which a pair of arms extends a resistance layer formed on the forked base, and a catalyst layer formed on one of the arms; outputting the change of the resistance value which originates in the reaction heat of oxidation of carbon monoxide contained in the gas by contacting with the catalyst layer of the resistance gas sensor; and calculating the carbon monoxide concentration of the gas from the output. The oxidation of carbon monoxide is activated by charging voltage to the resistance layer of the resistance gas sensor in order to heat the resistance layer.

BRIEF DESCRIPTIONS OF THE DRAWINGS

FIG. 1 is a plan view of a presently preferred embodiment of the resistance gas sensor used in the present invention;

FIG. 2 is a partial cross-sectional view of the detecting arm of the embodiment;

FIG. 3 is a partial plan view of terminals of the embodiment connected with electric wires;

FIG. 4 is a perspective view of the cylindrical holder of the embodiment;

FIG. 5 is a sectional view coinciding with line A—A' of FIG. 1, looking in the direction of the arrows;

DETAILED DESCRIPTIONS OF THE PREFERRED EMBODIMENTS

Figure 6:
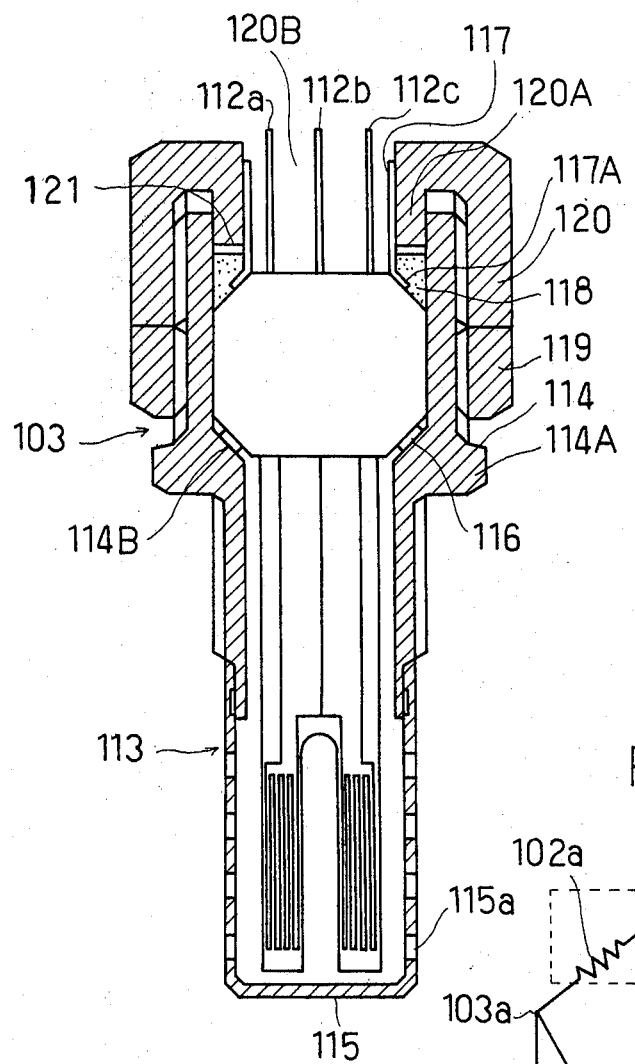
FIG. 6 is an elevational sectional view of the element of the embodiment held in the protector.

Referring now to the drawings, 101 is a forked base from which a pair of arms 101a extend. The forked base 101 is composed of a ceramic such as silica, chamotte, alumina, chromia, horsterite, spinel, chrome-magnesia, magnesium-chromia, carborumdum, zircon, zirconia, titania, cordillite, or the like. The ceramic preferably has a low thermal expansion coefficient and is heat resistant. Linear resistance layers 102a and 102b, which are respectively folded back at least one time, are formed on the surface of the arms 101a and 101b, as shown in FIG. 1. The resistance layers 102a and 102b preferably are composed of a material having good heat resistance and anticorrosive properties such as platinum, an alloy of platinum and rhodium, or the like. Except for their terminal ports, the resistance layers 102a and 102b are covered with a protecting layer 107. The protecting layer 107 may consist of a ceramic such as those mentioned above. The protecting layer 107 protects the resistance layers 102a and 102b from electrical shorts which otherwise could be caused by deposit of carbon contained in the exhaust gas on the surface of the resistance layers 102a and 102b. As shown in FIG. 2, the protecting layer 107 comprises an inner fine layer 107a consisting of ceramic particles having a particle size of 300 to 500 mesh and having a thickness of 5 to 15μ, and an outer coarse layer 107b consisting of ceramic particles having a particle size of 150 to 300 mesh and having a thickness of 10 to 20μ.

A catalyst layer 104 is formed on the protecting layer 107 of one of the arms 101a of the forked base 101. In the present embodiment, the catalyst layer 104 is in direct contact with the coarse layer 107b, so resistance to delamination between the catalyst layer 104 and the coarse layer 107b may be very large because of the coarse surface of the coarse layer 107b. As the material of the catalyst layer 104, a platinum group catalyst such as platinum, rhodium, palladium, an alloy of platinum and rhodium, or the like is preferably employed because of their effective catalysis on the oxidation of carbon monoxide. The catalyst is carried on the protecting layer 107 as a carrier in carrying amount of 3 to 10% by weight, and the thickness of the catalyst layer 104 may be in the range of 20 to 300μ.

Voltage is input to the resistance layer 102a and 102b through three terminals 103a, 103b, and 103c, and the change of the resistance value is also output from the resistance layers 102a and 102b through the terminals 103a, 103b, and 103c. Belt shaped leading wires 112a, 112b, and 112c are respectively connected to the terminals 103a, 103b, and 103c, as shown in FIG. 3. The leading wires 112a, 112b, and 112c may be composed of alloys having good anticorrosive properties such as hastelloy, inconelle, cormonoy, stainless steel, or the like. An electric conductive paint comprising an organic binder and an electric conductive metal powder such as platinum, gold, silver or the like is painted on the terminals 103a, 103b, and 103c, after which the leading wires 112a, 112b, and 112c are put upon them, and an electric conductive paste is painted over the leading wires 112a, 112b, and 112c. As the result, ohmic contact between the leading wires 112a, 112b, and 112c and the terminals 103a, and 103b, and 103c is provided.

The terminals 103a, 103b, and 103c are preferably protected by covering them with an organic adhesive layer 108. The inorganic adhesive layer 108 may be composed of a material chosen from the glass group, the polyphosphate group, the ceramics group, or the like. However, an adhesive from the ceramics group is most suitable in view of their anticorrosive properties.

The base 101 is to be inserted in a slit 110 of a cylindrical holder 109. The cylindrical holder 109 may be composed of the same kind of ceramic as the forked base 101. The edges of the two ends of the cylindrical holder 109 are formed into tapershapes 109a and 109b by cutting down, as shown in FIG. 4.

The above described element may be manufactured by the following method.

(1) Manufacturing the original forked base

An organic binder such as acrylic resin, vinyl acetate resin, styrene resin, or the like is added to a ceramic powder in the amount of about 10% by volume with an organic solvent such as toluol, xylol, ethyl acetate, n-butyl acetate, mineral spirit, or the like. The mixture is kneaded by a kneading apparatus such as a roll mill, a ball mill, a kneader, or the like. The mixture is then molded in a mold to form an original forked base, which may be a flexible sheet. An electrical resistance paint comprising a metal powder such as platinum, an alloy of platinum and rhodium, or the like, an organic binder such as acrylic resin, vinyl acetate resin, styrene resin, or the like, and organic solvent (such as toluol, xylol, ethyl acetate, n-butyl acetate, mineral spirit, or the like) is thick-film-printed on the surface of the original forked base by means such as silk-screen printing or the like to form the original linear resistance layers.

(2) Forming the original protecting layer

The above described original forked base is coated with a ceramic paint containing a ceramic powder having a particle size of about 300 to 500 mesh except the part of the forked base where the terminals are to be formed. After the coating the original forked base is dried to form an original fine layer. Next the original forked base is dipped in a slurry in which a ceramic powder having a particle size of about 150 to 300 mesh is suspended. After the dipping, the original forked base is dried to form the original coarse layer.

(3) Firing

An original cylindrical holder is manufactured by pre-firing a mold of the same kind of a ceramic powder as the original forked base is made from. The base of the original forked base is inserted into a slit in the original cylindrical holder, with the part of the base on which the terminals are to be formed extending outwardly from the original cylindrical holder. After the original forked base is inserted in the original cylindrical holder, they are fired at about 1600° C. for about 1 hour in atmosphere. The organic binder contained in the original base and holder is decomposed and in the removed from the original base and holder, and the ceramic powder is melted to adhere mutually by the firing. Thus the forked base 101, the resistance layers 102a and 102b, the protecting layer 107, and the cylindrical holder 109 are formed. The forked base 101 and the cylindrical holder 109 become one body.

(4) Forming the catalyst layer

A catalyst slurry containing a ceramic carrier carrying platinum group catalyst is coated on the arm 101a of the forked base 101 by dipping, painting, or the like, and the coated catalyst layer is dried at about 150° C. for about 2 hours. After the drying, the coated layer is fired at about 600° C. for 1 hour. Thus the catalyst layer 104 is formed on the arm 101a and the element S shown in FIG. 5 is manufactured.

The element S is contacted with the leading wires 112a, 112b, and 112c as described above, and the terminals 103a, 103b, and 103c, are then covered with the inorganic adhesive layer 108. The element S is then put in a protecting cover 113 as shown in FIG. 6.

The protecting cover 113 is composed of a holding tube 114 having a flange 114A in its middle part and a taper part 114B corresponding to the taper shape 109b of the cylindrical holder 109 in its inside and a cover 115 attached to the top of the holding tube 114. A number of ventilation openings 115a are formed in the cover 115. The element S is put into the protecting cover 113, and the arms 101a and 101b are positioned in the cover 115. In this position, the taper shape 109b of the cylindrical holder 109 is spaced from the taper part 114B of the holding tube 114 by a metal packing 116. Additionally, a cap 117 is inserted into the bottom of the holding tube 114. A taper part 117A of the cap 117 corresponding to the taper shape 109a of the cylindrical holder 109 is formed at the top of the inside of the cap 117. The taper part 117A of the cap 117 contacts the taper shape 109a of the cylindrical holder 109. A ceramic packing 118 is put around the taper part 117A of the cap and a metal packing 121 is put over the ceramic packing. Further, a nut 119 is screwed on the outside of the holding tube 114, and then a cap nut 120 having a flange 120A around a central opening 120B is screwed on the outside of the holding tube 114. Thus the element S is tightly fixed in the protecting cover 113 by the cap nut 120, since the flange 120A of the cap nut 120 presses the cylindrical holder 109 toward the taper part 114B of the holding tube 114.

As above mentioned, the reciprocal contacts of tapered shapes are preferably for tight fixing of the element S in the protecting cover 113 without rattling. The cap nut 120 is tightly fixed by screwing the nut 119 toward the cap nut 120 to prevent looseness of the cap nut 120.

The sensor assembled as aboved mentioned is arranged in a suitable position in the exhaust side of the engine to contact with the exhaust gas of the engine. It is preferable to adjust the arrangement of the sensor so that the forked base 101 of the element S faces the flow of the exhaust gas at a right angle. A voltage is charged to the resistance layers 102a and 102b through leading wires 112a, 112b, and 112c, and terminal 103a, 103b, and 103c to heat the forked base 101 to a temperature at which oxidation of carbon monoxide in the exhaust gas easily occurs. The temperature of the forked base 101 may be adjusted so as to prevent the self-combustion of hydrocarbon and carbon monoxide in the exhaust gas. The suitable temperature is in the range of about 250° C. to 300° C. due to the above mentioned considerations.

Figure 7:
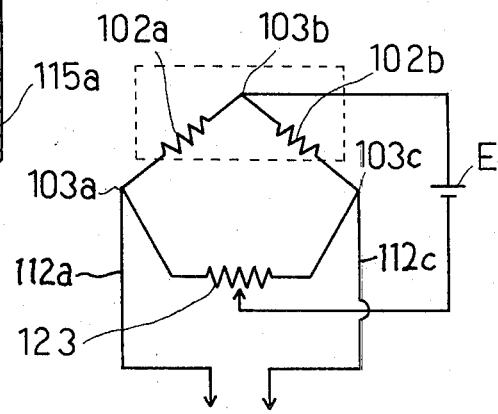
FIG. 7 is an electric circuit diagram employed in the embodiment.

The exhaust gas contacts with arms 101a and 101b of the forked base 101 through the ventilation openings 115a of the cover 115 of the protecting cover 113, and on the arm 101a the exhaust gas contacts with the catalyst layer 104 to oxidize carbon monoxide into carbon dioxide. The reaction heat of the oxidation increases the temperature of the resistance layer 102a of the arm 101a, while the standard temperature is maintained in the resistance layer 102b of the arm 101a, since it has no catalyst layer. Accordingly, a difference in the resistance value between the resistance layers 102a and 102b is produced. As shown in FIG. 7, the resistance layers 102a and 102b form a bridge circuit between an electric source E and a variable resistance 123. The variable resistance 123 is adjusted so as to keep the balance of the bridge circuit. When a difference is produced between the resistance layers 102a and 102b as above mentioned, the balance of the bridge circuit is lost, thereby changing the output voltage from the circuit. That change may be detected as the output of the sensor through leading wires 112a, 112b, and 112c. As the result, the EGR ratio may be controlled by the detected value.

As above mentioned, the structure of the sensor used in the instant invention may be very simple and easy to manufacture economically, since the resistance layer of the sensor may also act as a heater and accordingly forming the individual heater on the sensor is not necessary. Further, only terminals for the resistance layer are necessary, so the number of terminals may be decreased. Still further, decreasing number of terminals as above mentioned reduces the occurrence of the shorts.

We claim:
1. A resistance gas sensor comprising:
   (a) a forked base from which a pair of arms extend;
   (b) a resistance layer forming a resistive element in a bridge circuit disposed of each of said pair of arms, said resistance layers serving both to measure the difference in temperature between said arms and to heat a catalyst layer;
   (c) a protective layer means to prevent electrical shorts which might otherwise be caused by deposit of conductive particles contained in a gas to be detected on said resistance layers, said protective layer means comprising an inner protective layer formed from fine ceramic particles disposed over said resistance layers, and an outer protective layer formed from coarse ceramic particles disposed over said inner protective layer; and
   (d) a catalyst layer formed on one and only one of said pair of arms in direct contact with said outer protective layer, whereby:
   (e) when electricity is passed through said resistance layers, said resistance layers and said catalyst layer are heated
   (f) the change in the resistance value of said resistance layer on said one and only one of said pair of arms due to a reaction in a gas promoted by said catalyst layer can be used to calculate the concentration of the gas.
2. A resistance gas sensor as recited in claim 1 wherein said inner protective layer is formed from ceramic particles having a particle size of 300 to 500 mesh and have a thickness of 5 to 15μ.
3. A resistance gas sensor as recited in claim 1 or claim 2 wherein said outer protective layer is formed from ceramic particles having a particle size of 150 to 300 mesh and a thickness of 10 to 20μ.
4. A resistance gas sensor as recited in claim 1 wherein said catalyst layer has a thickness of 20 to 300μ.

* * * * *